United States Patent
Schrier et al.

(10) Patent No.: US 7,090,981 B2
(45) Date of Patent: Aug. 15, 2006

(54) CHICKEN ANAEMIA VIRUSES OF LOW PATHOGENICITY

(75) Inventors: Carla Christina Schrier, Boxmeer (NL); Henricus Johannes Maria Jagt, Venlo (NL)

(73) Assignee: Akzo Nobel N.V., Arnhem (NL)

( * ) Notice: Subject to any disclaimer, the term of this patent is extended or adjusted under 35 U.S.C. 154(b) by 168 days.

(21) Appl. No.: 10/772,020

(22) Filed: Feb. 3, 2004

(65) Prior Publication Data

US 2004/0157311 A1      Aug. 12, 2004

Related U.S. Application Data

(62) Division of application No. 09/793,873, filed on Feb. 27, 2001, now Pat. No. 6,723,324.

(30) Foreign Application Priority Data

Feb. 29, 2000    (EP)    ............................ 00200719

(51) Int. Cl.
*C12Q 1/68*    (2006.01)

(52) U.S. Cl. ............................ 435/6; 435/7.1; 435/345

(58) Field of Classification Search ............... 435/6, 435/7.1, 345
See application file for complete search history.

(56) References Cited

U.S. PATENT DOCUMENTS

| | | |
|---|---|---|
| 5,728,569 A | 3/1998 | Schrier |
| 5,914,113 A | 6/1999 | Schrier |

FOREIGN PATENT DOCUMENTS

| | | |
|---|---|---|
| EP | 0 533 294 A1 | 3/1993 |
| EP | 0 838 222 A1 | 4/1998 |

OTHER PUBLICATIONS

Yamaguchi et al: Journal of General Virology, 2000, 82, 1233-1238.
Immunology, Harper and Row, 1980, pp. 291-295.

*Primary Examiner*—Ali R. Salimi
(74) *Attorney, Agent, or Firm*—Aaron L. Schwartz; Williams P. Ramey, III

(57) ABSTRACT

The present invention provides a new antigenic type of chicken anaemia viruses (CAV). The CAV according to this invention is isolatable from turkeys in the field and its virulence for chickens is significantly reduced. This property makes these viruses particularly suited for preparing a live vaccine for protecting poultry against disease conditions resulting from CAV infection.

6 Claims, No Drawings

CHICKEN ANAEMIA VIRUSES OF LOW PATHOGENICITY

RELATED APPLICATIONS

This application is a divisional application of U.S. application Ser. No. 09/793,873, filed on Feb. 27, 2001, now U.S. Pat. No. 6,723,324. U.S. application Ser. No. 10/772,058, filed Feb. 3, 2004 (allowed) is also a divisional application of U.S. application Ser. No. 09/793,873.

The present invention relates to a chicken anaemia virus (CAV), a vaccine comprising a CAV and a method for the preparation of a CAV vaccine.

Chicken anaemia virus (CAV) is the causative agent of a disease known as avian infectious anaemia, anaemia dermatitis syndrome or blue-wing disease and was first described by Yuasa et al. in 1979 (Avian Diseases 23, 366–385, 1979).

Most outbreaks of naturally occurring CAV-induced disease have been reported in young chickens. The disease is acute and the first signs usually occur at 10–14 days of age. This clinical disease is characterised by a sudden increase in mortality, usually around 5–10%, but up to 60% has been reported. Peak mortality occurs within 5 to 6 days of onset of disease. Further clinical signs include depression and anorexia. Moreover, severe anaemia, haemorrhages throughout the body, atrophy of the thymus and bursa of Fabricius and yellowish bone marrow is seen in affected chickens (McNulty, Avian Pathol. 20, 187–203, 1991).

CAV spread both horizontally and vertically in chickens. When in-lay breeders with no previous exposure to the virus become infected, CAV is transmitted vertically to the progeny. No clinical signs are seen in the breeders and there is no apparent effect on egg production, hatchability or fertility. Vertically infected progeny chicks appear normal at hatching but showed increased mortality and develop typical disease (anaemia dermatitis syndrome) from 10 to 14 days of age. Horizontal spread occurs through contact with vertically infected chickens, contaminated fomites, houses, etc. Horizontal spread to young susceptible chickens that means without maternally derived antibodies to CAV may also lead to clinical disease two weeks later.

Ensuring that parent flocks develop antibodies to CAV before onset of lay can control the anaemia dermatitis syndrome. A high level of antibodies against CAV before the onset of lay will prevent vertical transmission during lay and will provide the off spring with maternally derived antibodies, which are protective during the first few weeks after hatching against horizontal infection.

Therefore, it is important that all birds are vaccinated with a CAV vaccine before the onset of lay.

Maternal antibody to CAV has usually disappeared by about 3 weeks of age. By that time horizontal infections can take place. These infections are normally sub-clinical, however this sub-clinical infection is associated with significant economic losses due to reduced growth of the broilers (McNulty et al., Avian Diseases 35, 263–268, 1991). The sub-clinical disease may be prevented by vaccinating the chickens immediately after hatch, preferably at one-day of age.

Clearly, a need exists for a safe vaccine that induces an effective protection against the clinical and sub-clinical disease associated with CAV infections. Because the possibility of spreading of vaccine viruses to susceptible flocks of young chickens exist in practise, live CAV vaccines for parent stock vaccination should be based on CAVs of low pathogenicity. Furthermore, as young chickens are very susceptible to CAV infection, live vaccines for direct administration to young chickens requires the availability of CAV isolates of low pathogenicity which do not adversely affect the young chicks.

However, all naturally occurring CAVs isolated so far are pathogenic for young chicks (McNulty, Avian Pathology 20, 187–203, 1991; Noteborn and Koch, Avian Pathology 24, 11–31, 1995; McNulty, British Poultry Science 38, 7–13, 1997). In addition, the attenuation of CAV isolates by in vitro passages in cell culture has resulted in ambiguous results. Bulow and Fuchs (J. Vet. Med. B 33, 568–573, 1986) reported a decrease of the pathogenicity of the Cux-1 isolate after 12 passages in MDCC-MSB1 cells which was further reduced after an additional 100–112 passages. However, Yuasa (Nat. Inst. Anim. Health Quarterly 23, 13–20, 1983) and Goryo et al. (Avian Pathology 16, 149–163, 1987) found no evidence of attenuation when CAV isolates were subjected to 19 and 40 cell cultures passages, respectively. Todd et al. (Avian Pathology 24, 171–187, 1995) demonstrated attenuation of the Cux-1 isolate by passages (173 times) in MDCC-MSB1 cells, but it was established that this attenuation was not stable and reversion to virulence occurred.

European patent application no. 0533294 discloses CAV isolates attenuated by passages in embryonated eggs. These isolates still display some rest-virulence for one-day-old chicks and, hence, are not particularly suited for vaccinating chicks younger than 1 week-of-age. In addition, these attenuated CAV isolates induce lesions in chicken embryos that make these vaccine viruses less suited for in ovo vaccination.

The chicken has been considered as the natural host for CAV. CAV was not found in a survey of UK turkey and duck sera and one-day-old turkey poults inoculated with CAV did not show clinical signs of anaemia and did not develop antibodies to the virus (McNulty et al., Avian Pathology 17, 315–324, 1988 and McNulty, Avian Pathology 20, 187–203, 1991). Only recently Farkas et al. (Avian Pathology 27, 316–320, 1998) reported that CAV antibodies were detected in a species (i.e. quail) other than chicken.

It is an object of the present invention to provide additional CAVs of low pathogenicity which can advantageously be used for the preparation of a live CAV vaccine, e.g. for broiler vaccination.

Another object of the present invention is to provide CAVs of low pathogenicity, in particular non-pathogenic CAVs which can be used for vaccinating birds most susceptible to CAV, e.g. for in ovo vaccination or vaccination of one-day-old birds.

It has now been found that these objects can be met by providing a chicken anaemia virus (CA), characterised in that the virus is neutralised by a reference sample comprising monoclonal antibody R2 secreted by a hybridoma cell line, a sample of which is deposited at the European Collection of Animal Cell Cultures (ECACC), Centre for Applied Microbiology & Research, Porton Down, Salisbury, Wiltshire SP4 OJG, UK, on Feb. 3, 2000 under accession no. 00020304.

Surprisingly, it has been found that naturally occurring strains of CAV of low pathogenicity exist. The CAVs according to this invention exhibit significantly reduced pathogenicity in one-day-old chickens if compared with naturally occurring CAV strains described so far, as determined by the ability of the virus to induce thymus atrophy, pale bone marrow and/or anaemia (Table 2). Similar unexpectedly, it has been found that these CAVs are isolatable from infected turkeys in the field.

The CAVs according to the invention are antigenically distinguishable from the hitherto known CAV strains isolated from infected chickens as well as from certain other CAV strains isolated from turkeys.

Monoclonal antibodies (Moabs) are useful for identifying characteristics of an infectious agent, and for determining antigenic similarities and differences among different isolates of the same or similar micro-organism. In Table 1 it is shown that the CAVs according to the present invention have a reaction pattern with a Moab which is different from that observed with known chicken strains or other turkey strains with a pathogenic character.

In particular it has been found that a CAV strain according to the invention is a virus that is neutralised by a sample comprising Moab R2, in contrast to the known CAV strains isolated from chickens that are not neutralised by this Moab.

To examine whether a CAV strain is neutralised by a sample comprising Moab R2, first the neutralising antibody titre of the Moab R2 sample against the CAV strain 319 deposited at the European Collection of Animal Cell Cultures (ECACC), Centre for Applied Microbiology & Research, Porton Down, Salisbury, Wiltshire SP4 OJG, UK, on Jan. 26, 2000 under accession no. V00012608 must be established in a virus neutralisation test, as described in Example 1 below. Depending on the antibody titre, a Moab R2 reference sample is prepared by either dilution or concentration of the Moab R2 sample so that 50 µl contains an antibody titre of 16 ($\log_2$) when examined against 300–1000 $TCID_{50}$ per 50 µl of CAV strain 319 in a virus neutralisation test as described in Example 1.

A CAV strain is considered to belong to the present invention when it is specifically neutralised in the virus neutralisation test by the Moab R2 reference sample. This means that in the virus neutralisation test the antibody titre of the Moab R2 reference sample is at least 5 ($\log_2$) per 50 µl when examined against 300–1000 $TCID_{50}$ per 50 µl of a CAV strain.

In particular, the present invention provides a CAV strain that is neutralised by higher dilutions of the Moab R2 reference sample. CAV strains that are neutralised by higher dilutions of the Moab R2 reference sample also exhibit a lower pathogenicity for chickens. Therefore, in a preferred embodiment of the invention a CAV strain is provided that is characterised by the fact that the antibody titre of the Moab R2 reference sample against that CAV strain is at least 10 ($\log_2$) per 50 µl, more preferably at least 12 ($\log_2$) per 50 µl or even at least 14 ($\log_2$) per 50 µl and particularly at least 16 ($\log_2$) per 50 µl when examined against 300–1000 $TCID_{50}$ per 50 µl of a CAV strain.

A CAV strain that is neutralised by higher dilutions of the Moab R2 reference sample is essentially non-pathogenic for young chickens and for chicken embryos. Therefore, such a CAV strain is particularly suited to be used in a live CAV vaccine for administration to chickens that are most susceptible for CAV infection, such as chicken embryos or one-day-old chickens.

A most preferred strain according to the present invention is CAV strain 319, a sample of which is deposited at the ECACC under accession no. V00012608. In view of its non-pathogenic properties this strain is particularly suited as a vaccine component for immunising young chickens or chicken embryos.

The identification of the new CAV strains according to the present invention allows the preparation of live CAV vaccines with low pathogenicity which can effectively protect poultry, in particular young chickens, against disease conditions resulting from the infection by the CAV. Therefore, in a preferred embodiment of this invention a CAV strain as defined above is provided that is in a live form.

Of course, the present invention also provides a CAV strain in inactivated from. The inactivated CAV strain can be used as a basis for an inactivated vaccine particularly suited for breeder vaccination.

A CAV according to the invention can also be isolated from turkeys in the field. Briefly, a serological survey of turkey sera collected from turkey flocks can be conducted to identify serum samples that are able to neutralise CAV in a standard virus neutralisation test. An example of such a survey is outlined in Farkas et al. (1998, supra). Subsequently, CAV can be isolated from organs of turkeys, as described in Example 1. Finally, a CAV according to the present invention can be identified by examining the reaction with the monoclonal antibody R2.

If desired, the CAVs of low pathogenicity characterised above can be adapted to embryonated eggs by passaging these CAVs in embryonated eggs such that the resulting viruses are able to grow to high titres in embryonated eggs. European patent application no. 0533294 discloses that the ability of a CAV to induce embryo lesions is associated with a growth advantage and further describes how such viruses can be obtained. Therefore, the present invention also provides CAVs of the above-mentioned type, which additionally have the property to induce lesions in chicken embryos. Such CAVs are suited for vaccination in ovo vaccination of embryos of 17 days and older or post-hatch vaccination of chickens of one-day-old or older.

The invention provides in a further aspect a vaccine for use in the protection of poultry against disease conditions, both clinical and sub-clinical, resulting from a CAV infection, comprising a CAV according to the present invention and a pharmaceutical acceptable carrier or diluent.

The CAV according to the present invention can be incorporated into the vaccine as a live or inactivated virus. However, the low pathogenicity of the present CAVs make these viruses particularly suited for incorporation in a live CAV vaccine.

A vaccine according to the invention can be prepared by conventional methods such as for example commonly used for the commercially available CAV vaccines. The preparation of veterinary vaccine compositions is also described in "Handbuch der Schutzimpfungen in der Tiermedizin" (eds.: Mayr, A. et al., Verlag Paul Parey, Berlin und Hamburg, Germany, 1984) and "Vaccines for Veterinary Applications" (ed.: Peters, A. R. et al., Butterworth-Heinemann Ltd, 1993).

Briefly, a suitable substrate is inoculated with a live CAV according to the invention and propagated until the virus replicated to a desired infectious titre or antigen mass content after which CAV containing material is harvested and formulated to a pharmaceutical composition with prophylactic activity.

Every substrate that is able to support the replication of the CAV defined above can be used to produce a vaccine according to the present invention. Suitable substrates include cell cultures, such as MDCC-MSB1 cells, chicken embryos and chickens for in vivo vaccine production.

For production on cell culture, the virus is usually propagated for 3–10 days after inoculation of the cells, after which the cell culture supernatant is harvested, and if desired filtered or centrifuged in order to remove cell debris.

Alternatively, the CAV according to the invention can be propagated in embryonated chicken eggs followed by harvesting the CAV material by routine methods such as described in European patent application no. 0533294.

The vaccine according to the invention containing the live CAV can be prepared and marketed in the form of a (frozen) suspension or in a lyophilised form. The vaccine additionally contains a pharmaceutically acceptable carrier or diluent customary used for such compositions. Carriers include stabilisers, preservatives and buffers. Suitable stabilisers are, for example SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the live vaccines according to the invention may contain an adjuvant. Examples of suitable compounds and compositions with adjuvant activity are the same as mentioned below for the preparation of inactivated vaccines.

Although administration by injection, e.g. intramuscular, subcutaneous of the live vaccine according to the present invention is possible, the live vaccine is preferably administered by the inexpensive mass application techniques commonly used for poultry vaccination. These techniques include drinking water and spray vaccination.

Alternative methods for the administration of the live vaccine include in ovo, eye drop and beak dipping administration.

As the present invention provides CAVs which are substantially non-pathogenic when administered in ovo in the last quarter of the incubation period, a particularly advantageous route for administrating a vaccine according to the present invention is the in ovo administration.

Usually, the vaccine is injected into embryonated eggs during late stages of the embryonation, generally during the final quarter of the incubation period (day 15–21), preferably at day 18 of the incubation period.

The mechanism of injection of the incubated eggs is not particularly critical provided that it does not unduly damage tissue and organs of the embryo. For example, a small hole is pierced with a needle (1–1½ inch, about 22 gauge) attached to syringe in the large end of the shell and the vaccine is injected below the inner shell membrane and the chorioallantoic membrane. Subsequently, the vaccinated embryonated eggs are transferred to an incubator to hatch (U.S. Pat. Nos. 4,458,630, 5,427,791, WO 98/56413 and WO 95/35121). Preferably, the whole embryo vaccination process is carried out using automated vaccination systems, such as the commercially available Inovoject®.

In another embodiment the present invention provides a vaccine against disease conditions resulting from CAV infection comprising the CAV in an inactivated form. The advantage of an inactivated vaccine is the elevated levels of protective antibodies of long duration that can be obtained. This property makes such an inactivated vaccine in particular suited for breeder vaccination. The preparation of an inactivated CAV vaccine according to the present invention can be obtained by routine methods well known to the person skilled in the art (such as described in European patent application no. 0533294).

A vaccine containing the inactivated CAV can, for example, comprise one or more of the above-mentioned pharmaceutically acceptable carriers or diluents suited for this purpose.

Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol F® or Marcol 52® or a vegetable oil such as vitamin E acetate, and saponins.

Inactivated vaccines are usually administered parenterally, e.g. intramuscularly or subcutaneously.

The vaccine according to the invention comprises an effective dosage of the CAV defined above as the active component, i.e. an amount of immunising CAV material that will induce immunity in the vaccinated birds or their progeny, against challenge by a virulent virus. Immunity is defined herein as the induction of a significant higher level of protection in a population of birds after vaccination compared to an unvaccinated group.

Typically, the live vaccine according to the invention can be administered in a dose of $10^2$–$10^9$ $TCID_{50}$ per bird, preferably in a dose ranging from $10^2$–$10^6$ $TCID_{50}$, and an inactivated vaccines may contain the antigenic equivalent of $10^4$–$10^{10}$ $TCID_{50}$ per bird.

Although, the CAV vaccine according to the present invention may be used effectively in chickens, also other poultry such as turkeys and quail may be successfully vaccinated with the vaccine. Chickens include broilers, reproduction stock and laying stock.

Because the clinical and sub-clinical disease conditions resulting from CAV infection, have been reported primarily in young chicks, in particular in broiler chickens, the present invention preferably provides a vaccine for use in the protection of broilers against CAV induced disease conditions.

The age of the animals receiving a live or inactivated vaccine according to the invention can be the same as that of the animals receiving the CAV vaccines presently known. Additionally, the low pathogenic character of the CAVs according to the present invention allows the administration of the CAV vaccine to young birds, i.e. less than two weeks of age, in particular to one-day-old birds or even to embryos by the in ovo route in the final quarter of the incubation period. For example, young birds, e.g. broilers, may be vaccinated directly from one-day-old onwards with the live vaccine according to the invention to prevent sub-clinical disease resulting from horizontal transmission of CAV. Vaccination of parent stock, such as broiler breeders, can be done with a live or inactivated vaccine according to the invention or with a protocol comprising a combinations of both vaccines. The advantage of these types of immunisation programmes includes the immediate protection of one-day-old progeny provided by maternally derived antibodies vertically transmitted to the young birds. A typical breeder vaccination programme includes the vaccination of the breeders from 6-weeks of age onwards with a live vaccine, or the vaccination between 14–18 weeks of age with an inactivated vaccine.

The present invention also provides a combination vaccine comprising, in addition to the CAV according to the invention, one or more vaccine components of other pathogens infectious to poultry.

Preferably, the combination vaccine comprises one or more (inactivated) vaccine strains of Mareks disease virus (MDV), infectious bronchitis virus (IBV), Newcastle disease virus (NDV), infectious bursal disease virus (IBDV), fowl adenovirus (FAV), EDS virus, turkey rhinotracheitis virus (TRTV), infectious laryngotracheitis virus (ILTV) and reovirus.

In particular, the present invention provides a live combination vaccine comprising a CAV according to the invention and a MDV vaccine strain, such as HVT. This combination vaccine can advantageously be used for in ovo vaccination.

EXAMPLES

Example 1

Isolation and In Vitro Identification of the CAV Strains with Low Pathogenicity

A

The CAV strains were isolated from organs derived from different turkeys according to the following procedure:

Organs were homogenised and centrifuged for 15 minutes at 3000 g. The supernatant was added to MDCC-MSB1 cells and subsequently, the suspensions were incubated at +37° C. After 2–3 days of incubation the cells were examined microscopically and subsequently, sub-cultured. This procedure was repeated until cyto-pathic effect (CPE) characteristic for CAV occurred. When CPE characteristic for CAV was present, the suspension was centrifuged for 15 minutes at 3000 g and subsequently the supernatant was harvested and stored at −70° C. Subsequent passages were produced according to the same procedure.

CAV chicken isolates were also multiplied in MDCC-MSB1 cells according to the procedure outlined above.

A further group of CAV strains according to the invention was isolated in a similar way from turkeys that were depressed due to unknown causes. Upon arrival the turkeys were sacrificed and their liver was removed. In the laboratory an equal volume of RPMI 1640 medium was added and subsequently a 50% liver homogenate was prepared by using an ultra turrax. After centrifugation for 10 minutes at 4000 g the supernatant was harvested through a 15 μm filter. The supernatant was stored at −70° C. until used for virus re-isolation attempts.

For the virus re-isolation attempts 0.2 ml of each of the liver supernatants was added to 30 ml of RPMI1640 medium (5% FCS) containing $3 \times 10^5$ MDCC-MSB1 cells per ml. After incubation for 2 or 3 days at +37° C. (5% $CO_2$) the MDCC-MSB1 cells were examined microscopically for the presence of CPE characteristic for CAV (large swollen cells with a clear cytoplasm). When CPE characteristic for CAV turned out to be absent, the cells were subcultured by adding 5 ml of the MDCC-MSB1 cell suspension to 25 ml of fresh RPMI 1640 medium (5% FCS). Subsequently, the cell suspensions were again incubated for 2 or 3 days at +37° C. (5% $CO_2$).

The MDCC-MSB1 cell suspensions were subcultured up to 10 times or until CPE characteristic for CAV was observed.

When CPE characteristic for CAV was observed the cell-virus suspension was harvested and centrifuged for 10 minutes at 4000 g. The supernatant was collected and stored at −70° C. until further use.

B

In a subsequent experiment it was examined whether the CAV strains according to the present invention could be distinguished from (known) chicken CAV strains and other turkey strains, by means of a virus neutralisation test, using monoclonal antibody R2, positive and negative polyclonal chicken serum directed to CAV.

Materials and Methods

CAV Strains
CAV chicken strain 26 P4 (wild-type and attenuated): EP patent application no. 0533294

CAV chicken strain Gifu (wild-type and attenuated): EP patent application no. 0533294

CAV chicken strain Angstrom: Angstrom et al., Avian Path. 17, 23–32, 1988

CAV chicken strain Cux: von Bülow et al., Zentralbl. Veterinarmed. 30, 742–750, 1983

CAV chicken strain Clone-1: Lamichane et al., Avian Dis. 35, 515–522, 1991

CAV chicken strain: Holland isolate, reference strain

CAV turkey strains 18938, SP6198, 18933, 17382, 319, 3571, 3533, 3527, 3570, 3572, 18012, 18936, 18010 and 18941.

Antibodies Directed to CAV

Moab R2

Positive CAV serum

Negative CAV serum

Virus Neutralisation Test

Starting with at least a 1:16 dilution, serial two fold dilutions of the Moab reference sample were made in a microtitre plate in tissue culture medium (RPMI 1640+5% FCS) ending up with 50 μl of each dilution (a positive and negative reference serum was included by using the same dilutions) Subsequently, an equal volume of either CAV suspension was added to each Moab R2 dilution.

In order to monitor the CAV infectivity titre in the neutralisation test simultaneously the CAV working dilution was titrated. Therefore, serial ten-fold dilutions ($10^{-1}$ to $10^{-4}$) of each CAV working dilution were prepared in tubes outside the microtitre plate. Subsequently, 50 μl of each dilution was transferred in twelve-fold into a microtitre plate. Another twelve wells of the same microtitre plate were filled with 100 μl of tissue culture medium to serve as negative control. Subsequently, 50 μl of tissue culture medium was added to the virus dilutions. The virus-Moab mixtures and virus dilutions of the titration were then incubated for an overnight period at +4° C. Subsequently, 100 μl of an MDCC-MSB1 cell suspension containing $6 \times 10^5$ cells was added to the virus-Moab mixtures and the virus dilutions and control of the titration. The microtitre plates were then transferred to an incubator (+37° C., 5% $CO_2$).

Following incubation for two to three days at +37° C., the cells included in the titration were examined for the presence of cytopathic effect (CPE) characteristic for CAV. When the titration revealed that less than 300 to 1000 $TCID_{50}$ of CAV per 50 μl was present, the cells included in the neutralisation test and in the titration were subcultured and again incubated for two to three days at +37° C. This procedure of incubation and subculturing of cells was performed until a CAV titre of 300 to 1000 $TCID_{50}$ per 50 μl was obtained in the titration. The CAV titres were calculated according to the method of Reed and Muench (The American Journal of Hygiene, 27, 493–497, 1937).

Antibody titres were determined by examining the cells added to the virus-Moab mixtures for the presence of CPE characteristic for CAV. The antibody titre ($\log_2$) is expressed as the reciprocal of the highest dilution of the Moab R2 reference sample at which CAV strains are neutralised completely i.e. no CPE characteristic for CAV is observed. When the antibody titre of the Moab R2 reference sample is <5 ($\log_2$) the particular CAV strain is considered not to be neutralised by Moab R2.

Results

TABLE 1

Log$_2$ antibody titres determined in the VN test

|  | R2 | CAV pos serum | CAV neg serum |
|---|---|---|---|
| Chicken strains | | | |
| CAV 26P4 (wild-type) | <4 | 13 | <4 |
| CAV 26P4 (attenuated) | <4 | 13 | <4 |
| CAF Gifu (wild-type) | <4 | 13 | <4 |
| CAV Gifu (attenuated) | <4 | 13 | <4 |
| CAV Cux-1 | <4 | 13 | <4 |
| CAV Angstrom | <4 | 12 | <4 |
| CAV Clone-1 | <4 | 13 | <4 |
| CAV Holland isolate | <4 | 11 | <4 |
| Turkey strains | | | |
| CAV SP6198 | <4 | 12 | <4 |
| CAV 319 | 16 | 11 | <4 |
| CAV 18938 | 16 | 12 | <4 |
| CAV 18933 | 14 | 10 | <4 |
| CAV 17382 | 7 | 10 | <4 |
| CAV 3571 | 16 | 11 | <4 |
| CAV 3533 | 16 | 12 | <4 |
| CAV 3527 | 16 | 12 | <4 |
| CAV 3570 | 16 | 12 | <4 |
| CAV 3572 | 16 | 12 | <4 |
| CAV 18012 | 16 | 12 | <4 |
| CAV18936 | 16 | 12 | <4 |
| CAV18010 | 16 | 12 | <4 |
| CAV18941 | 16 | 12 | <4 |

Conclusion

The virus neutralisation test revealed that a group of CAV turkey strains that exhibit a low pathogenicity for chickens can be distinguished from attenuated and pathogenic CAV chicken isolates and pathogenic turkey isolates (Table 1). The Moab R2 only neutralises the low pathogenic CAV strains isolated from turkeys, whereas it does not neutralise the pathogenic turkey isolate nor any of the known chicken strains. The results of the pathogenicity experiments are shown in Example 2.

Example 2

In Vivo Characterisation of the CAV Strains with Low Pathogenicity

A

In this experiment the CAV isolates were evaluated for their pathogenicity in SPF chickens. The pathogenicity of the CAV isolates was established by macroscopical examination of the thymus and bone marrow and by determination of the haematocrit (Ht) value.

Experimental Design

One-day-old SPF chickens were inoculated intramuscularly with $10^{6.0}$ TCID$_{50}$ of either CAV isolate. One group of chickens was not inoculated to serve as control. At 14 days of age, from each group a number of chickens were removed. Blood samples were collected for the determination of the Ht value. The thymus and bone marrow were examined macroscopically. The remaining chickens were kept four weeks of age. Before the start of the experiment and at four weeks of age blood samples were collected.

Sera were examined for the presence/absence of CAV antibodies by a virus neutralisation test as described above.

The actual infectivity titres of the preparations used for inoculation were determined by titration on MDCC-MSB 1 cells according to standard procedures. The virus-cell suspensions were sub-cultured every 2 to 3 days, up to 10 times. Subsequently, the end-point titre was determined by microscopical examination of the cells for the presence of CPE characteristic for CAV. The titre was calculated according to the method of Reed and Muench (1937, supra).

Results

The results of the macroscopical examination and haematocrit determination are summarised in Table 2.

The results of the serology are summarised in Table 3. No CAV antibodies could be detected in the sera derived from 10 one-day-old hatch mates. Also no CAV antibodies could be detected in the sera derived from the four-week-old control chickens.

TABLE 2

Results of macroscopical examination and Ht determination

| Inoculum | Actual infectivity titre administered (log$_{10}$ TCID$_{50}$) | % of chickens with thymus atrophy | % of chickens with pale bone marrow | % of chickens with anaemia (Ht < 27%) |
|---|---|---|---|---|
| Chicken strains | | | | |
| CAV Clone-1 | 6.0 | 79% | 50% | 21% |
| CAV Gifu | 5.8 | 100% | 100% | 67% |
| Turkey strains | | | | |
| CAV SP6198 | 4.9 | 100% | 93% | 20% |
| CAV 18938 | 4.9 | 40% | 0% | 0% |
| CAV 18933 | 5.3 | 0% | 0% | 0% |
| CAV 17382 | 6.6 | 53% | 27% | 7% |
| CAV 319 | 6.1 | 13% | 0% | 0% |

TABLE 3

Serology examination results:

| Inoculum | Mean log$_2$ CAV antibody titre at four weeks of age |
|---|---|
| CAV Clone-1 | n.d. |
| CAV Gifu | 12.0 (±0.0) |
| CAV SP6198 | 9.9 (±1.7) |
| CAV 18938 | 10.3 (±1.6) |
| CAV SP6198 | 9.9 (±1.7) |
| CAV 18933 | 10.8 (±1.3) |
| CAV 17382 | 10.2 (±1.5) |
| CAV 319 | 11.4 (±1.0) |

( ) = s.d.
n.d. = not done

Conclusion

The results obtained in this experiment show that the CAV strains according to the invention exhibit a reduced pathogenicity for chickens when compared to the CAV strains derived from chickens or other turkey strains.

B

In this experiment it was examined whether the CAV strains isolated from turkeys do induce embryo lesions characteristic for CAV. European patent application no. 0533294 discloses attenuated CAVs with reduced virulence for chickens. This advantageous property is associated with the property of these prior art viruses to induce lesions in embryonated eggs.

Experimental Design

Thirty fertilised SPF eggs were inoculated each with 0.2 ml of each CAV strain via yolk-sac route. The inoculum volume contained an infectivity titre of $10^{6.0}$ TCID$_{50}$. As positive control, 30 fertilised SPF eggs were inoculated with the attenuated CAV 26P4 strain, a CAV strain that is known to induce embryo lesions. Thirty fertilised SPF eggs, that were not inoculated, were included as negative control. Subsequently, the eggs were incubated in an egg incubator at +37° C. From 7 days of embryonated life onwards, the eggs were candled daily. Embryo death occurring up to 10 days of embryonated life was considered not being caused by CAV and therefore these eggs were discarded. Embryo death occurring from 11 days of embryonated life onwards was considered being caused by CAV and therefore embryos were harvested and examined macroscopically for the presence of lesions induced by CAV. At 17 days of embryonated life all remaining embryos were harvested and examined macroscopically for the presence of lesions induced by CAV.

Results

Embryo death is shown in Table 4.

TABLE 4

| Inoculum | No of eggs Inoc. | Embryo mortality Days of embryonated life | | | | | | | | | | |
|---|---|---|---|---|---|---|---|---|---|---|---|---|
| | | 7 | 8 | 9 | 10 | 11 | 12 | 13 | 14 | 15 | 16 | 17 |
| CAV 319 | 30 | 13 | 1 | — | — | 1 | — | — | — | 1 | — | — | — |
| CAV 18933 | 30 | 15 | 1 | — | — | — | — | — | — | — | — | — | — |
| CAV 18938 | 30 | 15 | — | — | 1 | — | — | — | 1 | — | — | — |
| CAV 26P4 Attenuated | 30 | 11 | — | — | 1 | — | — | — | 3 | 1 | — | 2 |
| Control Not inoc. | 30 | 3 | 1 | — | — | — | — | — | — | — | — | — |

Macroscopical Examination:

CAV Strain 319

The embryo that died at 14 days of embryonated life did not exhibit lesions characteristic for CAV. On macroscopical examination of the fourteen surviving 17-day-old embryos also no lesions characteristic for CAV were observed.

CAV Strain 18933

On macroscopical examination of the fourteen surviving 17-day-old embryos no lesions characteristic for CAV were observed.

CAV Strain 18938

The embryo that died at 14 days of embryonated life did not exhibit lesions characteristic for CAV. On macroscopical examination of the thirteen surviving 17-day-old embryos also no lesions characteristic for CAV were observed.

CAV 26P4 (Attenuated)

The embryos that died at 14, 15 and 17 days of embryonated life all exhibited lesions characteristic for CAV. On macroscopical examination of the twelve surviving 17-day-old embryos, lesions characteristic for CAV were observed in six embryos.

Conclusion

From this experiment it can be concluded that the naturally occurring CAV strains isolated from turkeys do not induce embryo lesions.

Example 3

In Ovo Vaccination

Experimental Design

Sixty 18-day-old embryonated SPF eggs were inoculated in ovo with 0.2 ml of either the commercially available CAV vaccine Nobilis strain P4 (EP 0533294), CAV strain 319 or embryo homogenate obtained from embryonated SPF eggs. A calculated infectivity titre of $10^{3.0}$TCID$_{50}$ was inoculated per egg. After inoculation the eggs were transferred to a hatch incubator and after hatch the chickens were placed in negative pressure isolators.

At 7, 14 and 21 days of age each time 5 chickens were removed from each group. Blood samples were collected for determination of haematocrit values. Subsequently, the chickens were sacrificed for post mortem examination. At post mortem examination the thymus and bone marrow were examined macroscopically.

At 6 and 8 weeks of age blood samples were collected from a number of chickens in each group and the sera were examined for the presence/absence of CAV antibodies.

For a period of eight weeks post hatch, chickens were observed daily for the occurrence of clinical signs of disease or mortality.

Materials and Methods

Virus Titration

The actual infectivity titres inoculated were determined by titration in MDCC-MSB1 cells according to standard procedures as described above.

Haematocrit Determination

Peripheral blood samples were collected in duplicate in heparinised micro-haematocrit (Ht) capillary tubes. Following centrifugation for 10 minutes at 15000 g, the haematocrit values were determined. Subsequently, the mean Ht value for each chicken was calculated. Chickens with values below 27% were considered anaemic.

Macroscopical Examination

Upon macroscopical examination, the percentage of affected animals with atrophy of the thymus and paleness of the bone marrow was determined.

Observations for Clinical Signs of Disease

Throughout the experiment, all chickens were observed daily for the occurrence of clinical signs of disease or mortality.

Serology

Serum samples were examined for the absence/presence of CAV antibodies using a competitive enzyme-linked immuno-sorbent assay (ELISA) with a solid phase bound CAV antigen, a CAV specific biotinylated monoclonal antibody and HRP coupled to avidin. Antibody titres (log$_2$) were the reciprocal of the highest serum dilution at which the biotinylated monoclonal antibody did not bind maximally. Serum samples with titres of <5 (log$_2$) are considered negative for CAV antibodies.

In ovo Inoculation

The blunt end of 18-day-old embryonated SPF eggs was swabbed with an iodine-solution to disinfect the surface. Subsequently, a hole was made in the eggshell by using a so-called egg-drill. The eggs were then inoculated with either virus dilution by using Discardit 1.0 ml syringes and Microlance orange 0.6×25 needles. Before transferring the eggs to a hatch incubator, the holes were sealed with paraffin.

CAV vaccine Nobilis Strain P4

At six weeks of age CAV antibodies were detected in 15 out of 17 sera examined. At eight weeks of age all seventeen chickens responded to CAV.

CAV Strain 319

At six weeks of age CAV antibodies were detected in 17 out of 18 sera examined. At eight weeks of age all eighteen chickens responded to CAV.

Negative Embryo Homogenate

At six and eight weeks of age no CAV antibodies could be detected in all sera examined.

Observation for Clinical Signs of Disease

Throughout the experiment no clinical signs of disease or mortality were observed in the chickens inoculated with strain P4, strain 319 or negative embryo homogenate.

Discussion

Following inoculation of 18-day-old embryonated eggs with CAV strain P4 or CAV strain 319, no clinical signs of disease or mortality were observed throughout the experiment. Determination of haematocrit values revealed that none of the chickens were anaemic. Serological examination revealed that the majority of chickens inoculated with CAV strain 319 or CAV strain P4 seroconverted to CAV at six weeks of age.

Macroscopical examination revealed that CAV strain P4 induced some slight to moderate thymus atrophy only at 14 days of age. However, CAV strain P4 did not induce changes of the bone marrow. Macroscopical examination further revealed that CAV strain 319 did not induce changes of thymus and bone marrow.

Conclusion

From this experiment it can be concluded that, following in ovo inoculation of 18-day-old embryonated SPF eggs, CAV strain 319 is less pathogenic for chickens than the attenuated CAV vaccine Nobilis strain P4.

Results

Infectivity Titration

The actual infectivity titres found in the inocula are listed below:

| | |
|---|---|
| CAV vaccine Nobilis strain P4 | $10^{1.9}$ $TCID_{50}$ per egg. |
| CAV strain 319 | $10^{2.9}$ $TCID_{50}$ per egg. |

Macroscopical Examination Results

The mean scores obtained at macroscopical examination are shown in table 5.

CAV vaccine Nobilis Strain P4

At 7 and 21 days of age no changes of the thymus were observed. At 14 days of age three chickens exhibited slight atrophy of the thymus and two chickens exhibited moderate atrophy of the thymus. At 7, 14 and 21 days of age no changes of the bone marrow were observed.

CAV Strain 319

At 7, 14 and 21 days of age no changes of both the thymus and bone marrows were observed.

Negative Embryo Homogenate

At 7, 14 and 21 days of age no changes of both the thymus and bone marrow were observed.

Determination of Haematocrit Values

The haematocrit values determined at 7, 14 and 21 days of age are shown in table 6. All haematocrit values determined were above 27%.

Serology

The mean CAV antibody titres are shown in table 7.

TABLE 5

Results of macroscopical examination

| | Percentage of pathological changes observed at x days of age | | | | | |
|---|---|---|---|---|---|---|
| | Bone marrow | | | Thymus | | |
| Inoculum | 7 | 14 | 21 | 7 | 14 | 21 |
| CAV vaccine Nobilis Strain P4 | 0% | 0% | 0% | 0% | 100% | 0% |
| CAV Strain 319 | 0% | 0% | 0% | 0% | 0% | 0% |
| Negative Embryo Homogenate | 0% | 0% | 0% | 0% | 0% | 0% |

TABLE 6

Haematocrit values.

| | Mean haematocrit values (%) determined at x days of age | | |
|---|---|---|---|
| Inoculum | 7 | 14 | 21 |
| CAV vaccine Nobilis Strain P4 | 33.0 (±1.0) | 34.6 (±2.3) | n.d. |
| CAV Strain 319 | 32.4 (±1.1) | 34.4 (±3.4) | 34.2 (±1.5) |
| Negative Embryo Homogenate | 32.4 (±1.1) | 34.2 (±1.6) | n.d. | n.d. = not done because all haematocrit tubes broke during centrifugation.
( ) = s.d.

TABLE 7

Serology results

| | Mean $log_2$ CAV antibody titre at x weeks of age | |
|---|---|---|
| Inoculum | 6 wks | 8 wks |
| CAV vaccine Nobilis Strain P4 | 6.5 (±1.4) | 7.8 (±1.2) |
| CAV strain 319 | 6.9 (±1.8) | 8.8 (±2.2) |
| Negative Embryo Homogenate | <4.0 (±0.0) | <4.0 (±0.0) |

( ) = s.d.

The invention claimed is:

1. A method for the preparation of CAV, comprising the steps of:
   a. inoculating a susceptible substrate with the CAV,
   b. propagating the virus, and
   c. harvesting CAV containing material, wherein the CAV is an isolated chicken anaemia virus (CAV), wherein the virus is neutralized by a reference sample comprising monoclonal antibody R2 secreted by a hybridoma cell line, having the identifying characteristics of a sample deposited at the ECACC under accession no. 00020304 and the virus is not a chicken anemia agent (CAA) virus attenuated by passaging wild type CAA virus in embryonated chicken eggs, wherein the virus induces lesions in chicken embryos, and wherein the antibody titre of the reference sample is at least 5 (log 2) per 50 µl when examined against 300–1000 $TCID_5$ per 50 µl of the CAV.

2. A method for the preparation of a vaccine for protecting poultry against disease conditions resulting from a CAV infection, comprising the step of combining the harvested CAV containing material prepared according to the method of claim 1 with a pharmaceutically acceptable carrier or diluent.

3. The method according to claim 1, wherein the titre of the reference sample against the CAV is at least 12 ($\log_2$) per 50 µl when examined against 300–1000 $TCID_{50}$ per 50 µl of the CAV.

4. The method according to claim 1, further comprising the step of inactivating the CAV.

5. The method according to claim 1 wherein the CAV has the identifying characteristics of the CAV strain 319, which is deposited at the ECACC under accession no. V00012608.

6. The method according to claim 1 wherein the CAV is CAV strain 319, which is deposited at the ECACC under accession no. V00012608.

* * * * *